US00PP36003P2

(12) United States Plant Patent
Hansen

(10) Patent No.: US PP36,003 P2
(45) Date of Patent: Jul. 9, 2024

(54) ***PENSTEMON* PLANT NAMED 'Rose Rhinestones'**

(50) Latin Name: *Penstemon barbatus*
Varietal Denomination: Rose Rhinestones

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,661

(22) Filed: Dec. 15, 2023

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
CPC ..... A01H 6/68; A01H 5/02
See application file for complete search history.

*Primary Examiner* — Keith O. Robinson

(57) ABSTRACT

The new and distinct cultivar of *Penstemon* plant named 'Rose Rhinestones' with strictly upright, tightly compact strong stems in a rounded mound, and numerous, deep rosy-colored flowers with a light pink throat and reddish veins for about four weeks beginning in early summer and repeating in late summer if deadheaded. The lanceolate foliage is bluish-green, and the plant is winter hardy to at least USDA zone 4. The new plant is useful in the landscape as a specimen plant, en masse or container plant, and attractive to hummingbirds.

2 Drawing Sheets

Botanical classification: *Penstemon barbatus.*
Variety denomination: 'Rose Rhinestones'.

STATEMENT REGARDING PRIOR DISCLOSURES UNDER 37 CFR 1.77(B)(6)

The first offer for sale was on Jan. 30, 2023, and the first sale was made by Walters Gardens, Inc. on Aug. 21, 2023, to N. Casertano Greenhouses and Farms, Inc. Walters Gardens, Inc. obtained the new plant and all information relating thereto, from the inventor. No plants of *Penstemon* 'Rose Rhinestones' have been sold anywhere in the world by any name nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct plant of Beardtongue, botanically known as *Penstemon* 'Rose Rhinestones' and will be referred to hereinafter also by its cultivar name 'Rose Rhinestones' and as the new plant. The new plant cultivar of Beardtongue is a hardy herbaceous perennial grown for landscape use.

*Penstemon* 'Rose Rhinestones' is a single seedling selection derived from a cross between the proprietary unreleased hybrid known only as 13-34-4 (not patented) as the female parent the proprietary unreleased hybrid known only as 13-7-2 (not patented) as the male parent on Jun. 9, 2016, at a wholesale perennial nursery in Zeeland, Michigan. Seed was collected in late summer of 2016. All subsequent evaluations were performed in a full-sun trial garden at the same nursery with loamy sand soil and irrigation and fertilizer as required. The individual seedling was assigned the breeder code 16-2-2 while being selected for further trials during the summer of 2017. The new plant was propagated by basal shoot cuttings at the same nursery in Zeeland, MI, and the original plant and the cuttings were evaluated over the next four years until final approval for introduction in the summer of 2021. The resultant asexually propagated cuttings have been stable and identical to the original plant in successive asexual propagations.

SUMMARY OF THE INVENTION

*Penstemon* 'Rose Rhinestones' differs from its parents as well as all other hardy Beardtongue known to the inventor in a combination of traits. The following characteristics in combination distinguish 'Rose Rhinestones' from all other Beardtongue plants known to the inventor:

1. Round mounded growth with tightly-compact strong upright stems;
2. Glaucous lanceolate foliage developing and maintaining a bluish-green coloration in high light intensity;
3. Flowering with numerous deep rosy-colored flowers with a light pink throat and reddish veins;
4. Flowers for four weeks beginning early summer in Michigan and repeating in late summer if deadheaded;
5. Winter hardy to at least USDA zone 4.

The nearest comparison cultivars are: 'TNPENHPI' U.S. Plant Pat. No. 31,500, 'P008S' (aka. RED ROCKS®) (not patented), 'Balquared' U.S. Plant Pat. No. 32,296, 'Cherry Sparks' U.S. Plant Pat. No. 28,869, 'Sunburst Ruby' (not patented), 'Pink Pearls' co-pending U.S. Plant patent application Ser. No. 18/445,662, 'Red Riding Hood' U.S. Plant Pat. No. 18,950, and 'Schooley's Coral' (not patented).

'TNPENHPI' has a shorter habit and the flowers are more purplish-red with a white inner corolla tube. 'P008S' has a slightly taller height, the flowers are slightly lighter rosy-red, broader with flatter labia lobes, and the inner corolla tube is nearly white. 'Balquared' has a taller habit, the peduncle is pubescent with a dark reddish color, the flower is broader, the flower aspect is more drooping, and the inner corolla tube is nearly pure white. 'Cherry Sparks' has a taller and broader habit, the outer flower color is slightly lighter reddish colored, and the inner corolla tube is white. 'Sunburst Ruby' has a taller habit, the foliage is smaller, narrower, and lustrous, the flowers are ruby-red with a white center, and the flowering is less dense. 'Pink Pearls' has a similar habit, but the flowers are lighter rose-colored. 'Red Riding Hood' has a taller habit and bright red flowers. 'Schooley's Coral' has a slightly taller habit, the initial buds are yellowish and turn pink just before opening to coral-pink flowers. In comparison with 'Balquared' and 'Red Riding Hood', the new plant proved more persistent and longer lived in the landscape.

The female has a taller habit and more salmon-colored flowers with narrower foliage. The male or pollen parent, 13-7-2, has more reddish flowers.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, temperature, and direction may cause the appearance of minor variations in color. The plants used in the photograph are two-year-old plants grown in full sun field in loamy sand soil in trial gardens of a nursery in Zeeland, Michigan.

DETAILED BOTANICAL DESCRIPTION

Figure 1:
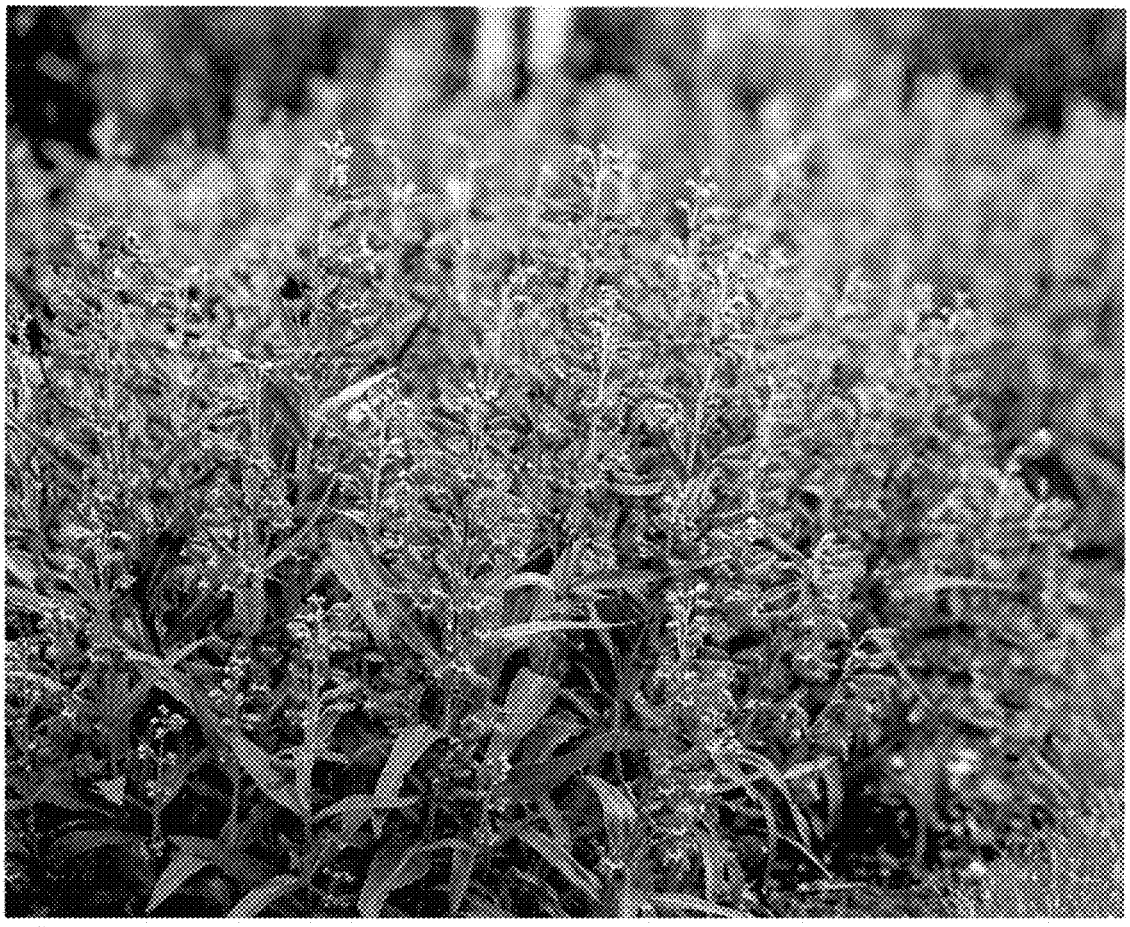
FIG. 1 shows the new plant in a trial garden landscape in early flower production.
Figure 2:
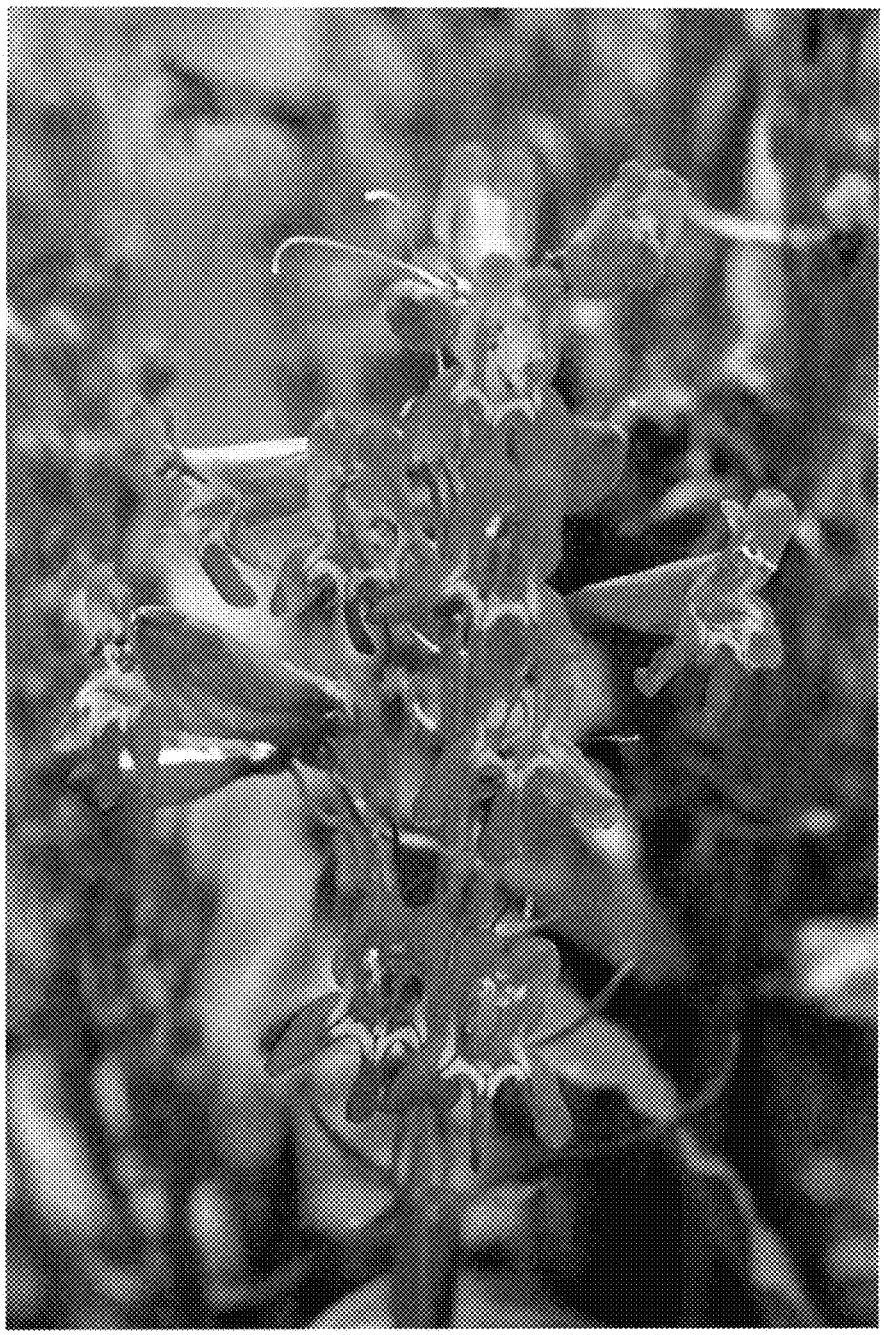
FIG. 2 shows a close-up of the flowers and buds.

The following is a detailed description of *Penstemon* 'Rose Rhinestones' as observed and compared to other cultivars for two years in trial gardens and production fields at a nursery in Zeeland, Michigan. The following description is of a two-year-old plant growing in a full-sun display garden in Zeeland, MI with limited supplemental fertilizer and irrigation as needed and without any pinching or plant growth regulators. The new plant has not been observed under all possible environments, and the phenotype may vary slightly with different environmental conditions, such as temperature, light, fertility, moisture, and maturity levels, but without any change in the genotype. The color descriptions are in accordance with the 2015 edition of The R.H.S. Colour Chart of The Royal Horticultural Society, London, England, except where common dictionary color terms are used.

Parentage: The female (seed) parent is 13-34-4 and the male (pollen) parent is 13-7-2;

Plant habit: Herbaceous winter-hardy, perennial with upright rigid stems emerging from the base in the spring; up to about 16 stems per plant; flowering in branched panicle;

Plant size: About 35 cm in height, average stem 29 cm tall, and about 32 cm in width about 10 cm above the soil;

Root description: Fibrous, well-branched, developing to about 1 mm thick; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 3.8-liter pot from a rooted plug;

Stem description: Terete; oppositely branched in the distal region; glabrous; glaucous; to about 30 cm long and about 6 mm diameter at base;

Stem color: Between RHS 138A and RHS N138B;

Node: About 4 per stem below flowers, average internode length about 4.2 cm, larger distally; Internode color: same as surrounding stem;

Foliage description: Simple; lanceolate; glabrous and slightly glaucous adaxial and abaxial; sessile with attenuate base; margin entire; fragrance not detected;

Leaf size: Leaves to about 154 mm long and about 25 mm wide;

Leaf color: Young expanding adaxial and abaxial between RHS N138A and RHS 132A; mature adaxial between RHS N138A and RHS 133B, abaxial nearest RHS N138C;

Leaf venation: Pinnate;

Petiole: Absent;

Vein color: Young abaxial midrib nearest RHS 158C with slight blush of nearest RHS 70B in basal 1 cm then distal one-third to one-half RHS 187C, young abaxial secondary veins RHS 187C; young adaxial midrib nearest RHS N138B, secondary veins between RHS N138A and RHS 133B; mature abaxial and adaxial midrib and secondary veins nearest RHS 187A;

Inflorescence: Panicle; flowering portion to about 18 cm long and about 7 cm across; with up to 54 flowers per inflorescence;

Pedicel: Cylindrical; glabrous, lustrous; size in length, between 5 and 10 mm long, and 1 mm diameter;

Pedicel color: Nearest RHS 146D;

Peduncle: Branched panicle with up to twelve branches; smooth, glabrous; main stems vertical; to about 35 cm tall and 6 mm diameter base flowering in upper 18 cm; to about 54 flowers per stem and 10 flowers per branch;

Peduncle color: Between RHS 146D and RHS 147C;

Flower buds about one day prior to opening: About 29 mm long, about 7 mm wide distally, and 3 mm diameter near the base; clavate; rounded apex; basal 3 mm of corolla tube narrowed to about 3 mm diameter, with rounded base;

Bud color: Dorsal labium proximal 4 mm nearest RHS 145D, next 4 mm nearest RHS 53A, and distally between RHS 46C and RHS 53C, ventral portion proximally nearest RHS 145D, distal portion between RHS 46C and RHS 53C, and middle portion nearest RHS 51A with veins of nearest RHS 71A;

Flowering season: Beginning in early June to early July and flowering for about five weeks, repeating if deadheaded;

Flowers: Zygomorphic; perfect; complete; bilabiate with upper and lower lip gamopetalous in about basal 21 mm; about 32 mm long and about 14 mm across and 16 mm tall at the face; face flat when first open becoming slightly reflexed and longitudinally folded in ventral lobes; lasting about five to seven days;

Flower attitude: Mostly outward;

Flower fragrance: None detected;

Corolla: Bilabiate; ventral petal with three lobes; dorsal petal with two lobes; glabrous abaxial; glabrous adaxial dorsal petal and fused tube portion, except pubescent on an adaxial ventral petal in the distal portion near mouth; dorsal petal lobes about 3 mm long and 5 mm across at fusion with rounded apices; two ventral lobes side lobes about 8 mm long and 5 mm wide at division just beyond midpoint between fusion and apex, center ventral lobe about 8 mm long and 4 mm across; all lobes with rounded apices and entire margins; corolla tube about 21 mm long, 14 mm wide and 16 mm tall at fusion and 4 mm diameter at base;

Corolla color: Dorsal labium adaxial basal 3 mm of corolla tube nearest RHS 145D, next 4 mm between RHS 53A and RHS 60B, young center corolla nearest RHS 49B and lobes between RHS 53B and RHS 53C, mature center corolla variable nearest RHS 64B and nearest RHS 62D with lobes between RHS 64A and RHS 64B; dorsal abaxial basal 3 mm nearest RHS 145D, next 3 mm between RHS 53A and RHS 60B, distally nearest RHS 53C when young and maturing to between RHS 60C and RHS 64B; dorsal labium young abaxial basal 3 mm nearest RHS 145D, next 3 mm nearest RHS 61B, middle portion between RHS 63D and RHS 62D with veins of between RHS 59B and RHS 71A, and lobes of between 53B and RHS 53A; ventral labium adaxial basal 3 mm nearest RHS 145D, next 3 mm nearest RHS 61B, young middle portion between RHS 63D and RHS 62D with veins between RHS 59B and RHS 71A, lobes between RHS 53B and RHS 53A, and pubescent region nearest RHS 65D, mature middle portion nearest RHS 63D with veins nearest RHS N79B, pubescent region nearest RHS 64C, and lobes nearest RHS 64B; ventral labium abaxial basal 3 mm nearest RHS 145D, next 3 mm between RHS 53A and RHS 6B, young distal region and lobes between RHS 67A and RHS 64B, mature distal region and lobes nearest RHS 64A;

Gynoecium: Single; superior; persistent after corolla drops; about 27 mm long;

*Style*.—Cylindrical; glabrous; arcuate slightly downwardly distally; about 21 mm long and about 0.5 mm diameter; color nearest RHS NN155B developing to nearest RHS 64B after corolla drop.

*Stigma*.—Semi-globose, to about 0.5 mm diameter; color nearest RHS NN155A.

*Ovary*.—Oblong conical; with truncate base and acute apex; about 6 mm long and 2 mm across at base; color nearest RHS 146D.

Androecium: Four; didynamous; slightly arcuate;

*Filaments*.—Longer set about 28 mm long and adnate inner corolla in basal 13 mm, shorter set about 25 mm long adnate inner corolla in basal 3 mm, about 1 mm in diameter; color nearest RHS NN155B.

*Anther*.—Elliptic; basifixed; longitudinal; bent at filament attachment; about 4 mm long and 1.5 mm across; color nearest RHS 11C.

*Staminode*.—Single; cylindrical; about 24 mm long and 0.5 mm diameter; adnate to inner corolla tube in basal 8 mm; tufted in distal 2 mm.

*Staminode color*.—Basal 4 mm between RHS 145D and RHS 155C, distally nearest RHS NN155B.

*Pollen*.—Abundant; color nearest RHS NN155B.

Calyx: Campanulate; adpressed to corolla; about 7 mm long and about 6 mm across at apex;

Sepals: Five; lanceolate; glabrous adaxial and abaxial; acute apex and fused in basal 2 mm; entire margin; to about 3 mm wide above fusion point and 7 mm long;

Sepal color: Adaxial and abaxial between RHS 137D, RHS 138A and RHS 146B with margins between RHS 145D and RHS 155C;

Fruit: Septicidal capsule; ovoid with acute apex and rounded base; to about 11 mm long and 4 mm across; color with maturity nearest RHS 199C;

Seed: Irregular; flattened, dried; about 2 mm across and about 0.3 mm thick; color nearest RHS 200A;

Hardiness to at least U.S.D.A. zones 4 to 8: The new plant performs best with good drainage and is resistant to drought once established;

Pest and disease resistance: Resistance beyond that typical of Beardtongue plants has not been observed. No other susceptibility or resistance to diseases or pests has been observed except that which is common to *Penstemon*.

It is claimed:

1. A new and distinct cultivar of *Penstemon* plant named 'Rose Rhinestones' as herein described and illustrated.

* * * * *